United States Patent [19]

Karcher et al.

[11] Patent Number: 4,697,574
[45] Date of Patent: Oct. 6, 1987

[54] PUMP FOR ASSISTANCE IN CIRCULATION

[75] Inventors: Gilles Karcher, Nancy; Max Amor, Vandoeuvre; Roger Niddam, Le Rancy; Jean-Pierre Villemot, Nancy, all of France

[73] Assignee: Medicorp Research Laboratories Corp., Boca Raton, Fla.

[21] Appl. No.: 831,349

[22] Filed: Feb. 20, 1986

[30] Foreign Application Priority Data

Feb. 20, 1985 [FR] France ................... 85 02428

[51] Int. Cl.⁴ ............................................. A61B 19/00
[52] U.S. Cl. ..................................... 128/1 D; 604/99; 604/118; 604/120
[58] Field of Search ............... 128/1 D, 695, 697, 687, 128/688, 784, 785, 786, 419 P; 604/99, 101, 118–120

[56] References Cited

U.S. PATENT DOCUMENTS

| 3,692,018 | 9/1972 | Goetz et al. | 128/1 D |
| 3,707,960 | 1/1973 | Freed | 128/1 D |
| 3,937,225 | 2/1976 | Schramm | 128/785 |
| 4,519,403 | 5/1985 | Dickhudt | 128/785 |
| 4,522,195 | 6/1985 | Schiff | 128/1 D |
| 4,527,549 | 7/1985 | Gabbay | 128/1 D |
| 4,531,936 | 7/1985 | Gordon | 128/1 D |
| 4,546,759 | 10/1985 | Solar | 128/1 D |
| 4,574,807 | 3/1986 | Hewson et al. | 128/786 |
| 4,598,697 | 7/1986 | Numazawa et al. | 128/1 D |

Primary Examiner—C. Fred Rosenbaum
Assistant Examiner—Gene B. Kartchner
Attorney, Agent, or Firm—Darby & Darby

[57] ABSTRACT

A first balloon 11 plugs the aorta 1 during the diastole, upstream of the supraaortic arteries 2, 3. A second balloon 12 insures a propulsion of blood toward the coronaries 6,7. A pump 8 commands the inflation and deflation of the balloons from signals from an ECG and a pressure sensor 13 placed opposite the coronaries 6,7.

7 Claims, 2 Drawing Figures

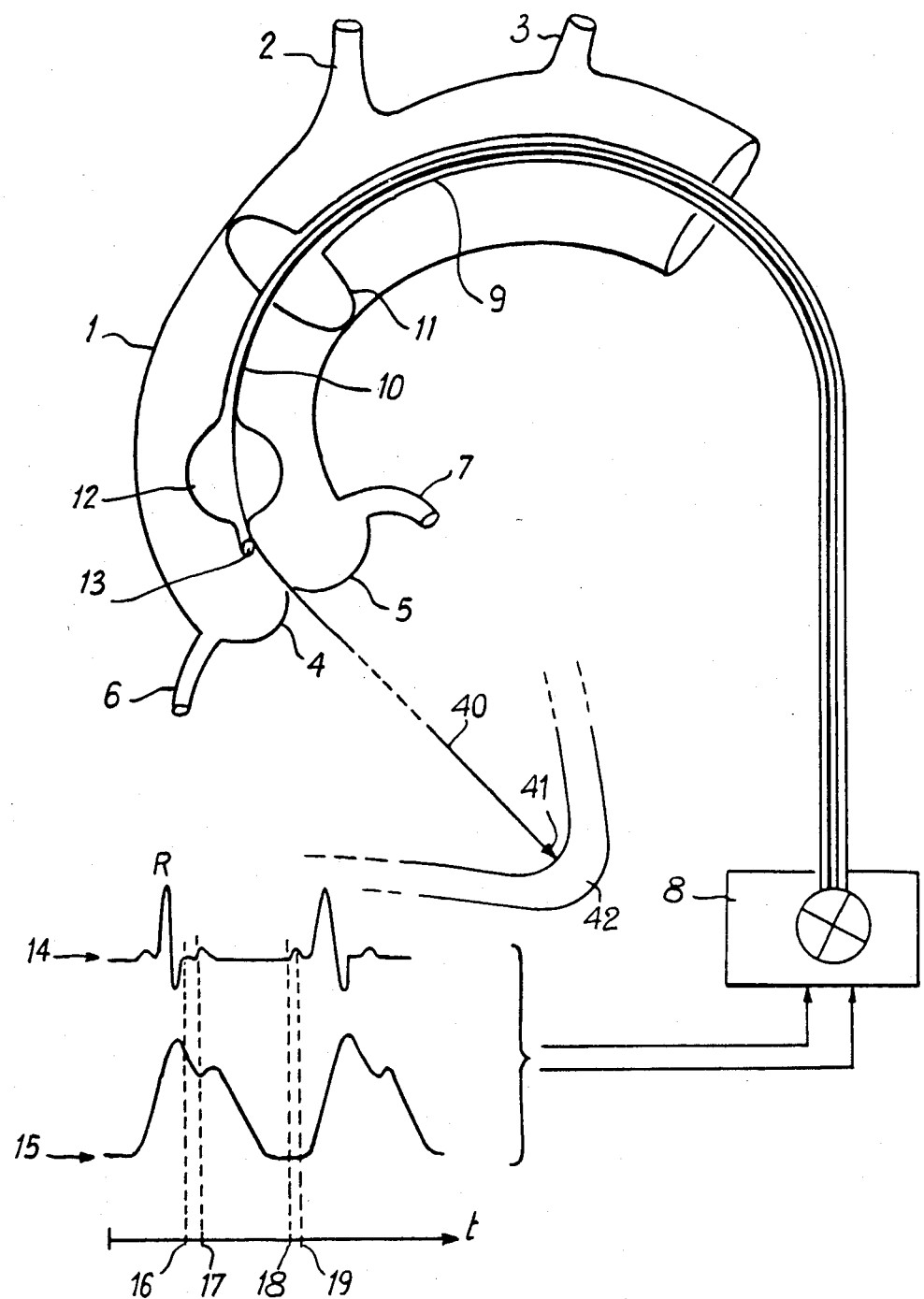

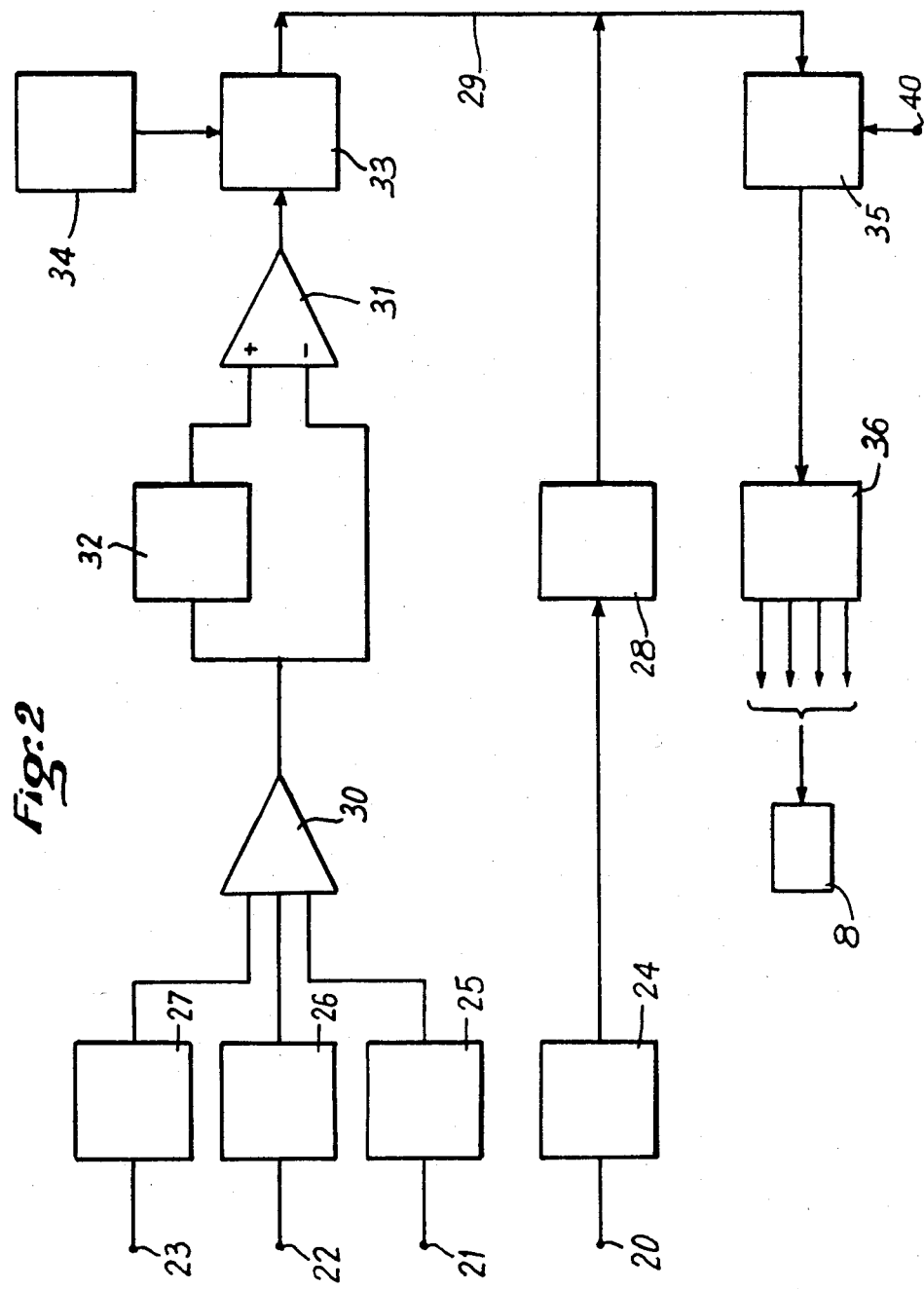

PUMP FOR ASSISTANCE IN CIRCULATION

The invention relates to a circulatory and coronary assistance pump with intra-aortic balloons.

In certain situations of cardiac insufficiency, pre- or postoperatory, it is indispensable to assist the cardiac function, in particular to insure better coronary circulation. For this purpose it is in the state of the art to use the so-called system of counter propulsion by intra-aortic balloon. A balloon placed in the descending aorta is inflated and deflated under the control of the electrocardiogram (ECG), so as to increase the intra-aortic diastolic pressure and as a consequence the coronary perfusion pressure.

But since the balloon is placed far from the heart, and in particular, downstream of the supra-aortic trunks, it has little influence on the coronary situation, which can actually be the cause of the weakness of the cardiac output. Moreover, this balloon is quite large and it requires a sound of large diameter, hence a rigid and bulky one. And finally, the control of the balloon as a function of the cardiac rhythm has gaps.

A first aim of the invention is to propose a coronary assistance pump which acts as close as possible to the coronary arteries and causes the least possible trauma to the organism.

Another aim of the invention is to provide a balloon control that will be free of the parasites to which the electrocardiogram is subject.

The subject of the present invention is a circulatory and coronary assistance pump with intra-aortic balloons utilizing the signals from an electrocardiogram (ECG) to command the inflation of the ballons during the diastole, characterized in that it comprises: a first sound terminating in a first aortic obturation balloon; a second sound terminating in a second propulsion balloon; the said second sound bearing, at its end, a sensor of the pressure prevailing in the aorta opposite the cardiac valves, a guide whose end is fixed in the apex of the left ventricle to insure the mooring of the sounds and balloons; and a pump providing sequences of inflation and deflation of the two balloons by means of the sounds under the control of an electronic circuit, taking into account both the signals from the ECG and the signals from the pressure sensor.

According to other characteristics of the invention:
the first balloon is placed in the ascending aorta upstream of the supra-aortic trunks, and the second balloon upstream of the first balloon, opposite the coronary arteries so that the inflation of the first balloon insures the blocking of the aorta, and that of the second balloon, a propulsion toward the coronary arteries of a volume of blood substantially equal to the volume of the second balloon.
the electronic circuit comprises, for the command of the pump, a micro-processor receiving: a measurement of the time elapsed since the last R wave of the ECG, a digital measurement of the momentary pressure in the aorta at the point of the sensor, and a measurement of the endo-cavitary potential,
the measurement of the momentary pressure is obtained by means of an analog/digital converter whose sampling frequency is on the order of 100 to 500 per second,
the measurement of the time elapsed since the last R wave of the ECG is obtained by means of a counter that counts the pulses of a clock and is reset to zero by the synchronous pulse of the R wave of the ECG,
the synchronous pulse of the R wave of the ECG is the output pulse from a comparator receiving at its − input a signal corresponding to the sum of the signals of the first three usual derivations of an ECG, and at its + input the mean value of the said signal obtained by an integrator.
the guide insures the measurement of the endo-cavitary potential, and perhaps a stimulation of the heart.

Other characteristics will appear on reading the description which follows given in reference to the attached drawing in which:

FIG. 1 is a simplified diagram of the principle of embodiment of the circulatory and coronary assistance pump according to the invention.

FIG. 2 is a simplified symbolic diagram of an embodiment of the electronic circuit commanding the pump in FIG. 1.

Referring to FIG. 1 we can see an aorta 1 and the start of the supra-aortic trunks of the right 2 and the left 3. The cardiac mass is not shown and is symbolized by the cardiac valves 4, 5 and the coronary arteries of the right 6 and left 7.

The assistance pump is schematized at 8. It can supply gas, for example, to two sounds 9 and 10, which are shown as coaxial but can be disposed in any suitable manner. Each of these two sounds terminates in an inflatable balloon: sound 9 in the first balloon 11, or obturation balloon; sound 10 in the second balloon 12, or propulsion balloon. And finally, sound 10 bears at its end, beyond balloon 12, a pressure sensor 13 situated just opposite the cardiac valves 4 and 5.

A guide 40 is also provided to insure a certain rigidity for the sounds 9 and 10. This guide terminates in an end 41 which is fixed in the apex of the left ventricle, symbolized at 42. The fixation must be made retractable because the assistance pump is put in place temporarily. Guide 40 has three functions. First it insures the mooring of the balloons and the sounds in the ascending aorta. It thus avoids the displacement of the balloons under the influence of the systolic blood flow. Then, it insures a detection of the endo-cavitary potential, which provides independence of the parasites and disturbances in the conduction to command the synchronization of the operation of cardiac assistance. And finally, it can play the usual role of cardiac stimulator in case of need.

The obturation balloon 11 is placed upstream of the carotid arteries, in the ascending aorta. When it is inflated it plugs the aorta and isolates a cavity upstream which extends to the valves 4, 5. Propulsion balloon 12 is placed upstream of balloon 11 in the ascending aorta and opposite the coronary arteries 6 and 7.

The assistance pump works as follows, and it intervenes during the diastole: pump 8 inflates balloon 11 through sound 9 until the aorta is plugged; it then inflates balloon 12 through sound 10, making it possible to send into coronary arteries 6 and 7 a required volume of blood which corresponds substantially to that of balloon 12. Then the balloons are deflated before the systole and the cycle begins again with the next diastole.

FIG. 1 schematizes the representative signals as a function of the time t, of an electrocardiogram 14 and of the pressure 15 prevailing in the aorta at the level of the pressure sensor 13. On the time scale we note that the inflation of the first balloon 11 intervenes at point 16, that of the second balloon 12 intervenes at point 17, while the deflation of the first balloon 11 intervenes at point 18 and that of the second balloon 12 at point 19.

The selective inflation of the balloons should be triggered at the start of the diastole, and the deflation at the end of the diastole so as not to interfere with the blood circulation in the aorta. The sequence of inflation of the balloons and the corresponding synchronization of the operations is very important for the hemodynamic efficiency of this system of circulatory assistance. This is why this synchronization is insured both on the signals from an ECG and on the pressure signals furnished by sensor 13.

The electronic circuit commanding pump 8 is represented in FIG. 2. The pressure signal arrives at 20 and the signals from the first three classic derivations of an electrocardiogram, ECG 1, ECG 2, ECG 3 arrive, respectively at 21, 22 and 23.

The four signals 20 to 23 are subjected to filtration in the low-pass filters 24 to 27. The pressure signal is then subjected to an analog/digital conversion in a converter 28 whose sampling frequency is on the order of 100 to 500 per second. The corresponding digital signal is applied to a bus-bar 29.

The three ECG signals are processed so that the R waves are in the positive direction and, at the outlet from filters 25 to 27 they are applied to a summator 30. The output signal from summator 30 is applied on the one had directly to the − input of a comparator 31, and on the other hand, through an integrator which provides the mean value, to the + input of the comparator 32. Thus the comparator continuously compares the momentary value of the signal with its mean value, and it delivers an output pulse only during the interval of time when the R wave exceeds the mean value of the signal. This output pulse from comparator 31 is applied to the zero reset input of a counter 33. This counter continuously counts the pulses from a clock 34 and it transmits to bus-bar 29, the numbers corresponding to the time elapsed since the last R wave which reset the counter to zero. Bus-bar 29 then transmits to a microprocessor 35, on the one hand a measurement of the time elapsed since the last R wave from the ECG and on the other hand a digital measurement of the momentary pressure in the aorta at the point of the sensor 13.

The microprocessor 35 also receives, from guide 40, a measurement of the endo-cavitary potential and it commands, through an output module 36, the openings and closings of the pump 8 correspondings to the points 16 to 19 of inflation and deflation of balloons 11 and 12.

By taking into account the ECG signals, the signals of pressure in the aorta and the endo-cavitary potential, the electronic circuit commanding pump 8 provides relief from the parasites to which the ECG's are subject. The circulatory and coronary assistance insured by the pump according to the invention therefore prove to be particularly effective.

We claim:

1. Circulatory and coronary assistance pump with intra-aortic balloons, utilizing the signals from an electrocardiogram (ECG) to command the inflation of the balloons during the diastole, comprising: a first sound (9) terminating in a first balloon (11) to plug the aorta (1); a second sound (10) terminating in a second propulsion balloon (12); the said second sound (10) bearing at its one end a sensor (13) of the pressure prevailing in the aorta opposite the cardiac valves, a guide (40) attached to said first and second sounds (9,10), said guide (40) having an end (41) which is fixable in the apex of the left ventricle (42) for insuring the mooring of the sounds (9,10) and the balloons (11,12) for insuring detection of the endo-cavitary potential, and for providing capability of cardiac stimulation; and a pump (8) connected to one and the other ends of said first and second sounds, (9,10), respectively, for insuring, in sequence, the inflation and deflation of the two balloons (11,12) through the sounds (9,10) under the control of an electronic circuit that takes into account both the signals from the ECG and the signals from the pressure sensor.

2. The circulatory and coronary assistance pump according to claim 1, further including means for locating said first balloon (11) in the ascending aorta upstream of the supra-aortic trunks, and means for locating the second balloon (12) upstream of the first balloon, opposite the coronary arteries (6,7) whereby inflation of the first balloon (11) provides plugging of the aorta, and inflation of the second balloon (12) causes a propulsion toward the coronary arteries (6,7) of a volume of blood substantially equal to the volume of the second balloon.

3. Pump according to claim 1, characterized in that the electronic circuit comprises, for the command of the pump (8), a microprocessor (35) receiving a measurement of the time elapsed since the last R wave of the ECG, a digital measurement of the momentary pressure in the aorta at the poin of the sensor (13) and a measurement of the endo-cavitary potential.

4. Pump according to claim 3, characterized in that the measurement of the momentary pressure is obtained by means of an analog/digital converter whose sampling frequency is on the order of 100 to 500 per second.

5. Pump according to claim 3, characterized in that the measurement of the time elapsed since the last R wave of the ECG is obtained by means of a counter (33) which counts the pulses of a clock (34) and which is reset to zero by a synchronous pulse from the R wave of the ECG.

6. Pump according to claim 5, characterized in that the synchronous pulse from the R wave of the ECG is the output pulse from a comparator (31) which receives, at its − input a signal corresponding to the sum of the signals from the first three usual derivations of an ECG, and at its + input the mean value of the said signal obtained by an integrator (32).

7. Pump according to claim 3, characterized in that the guide (40) insures the measurement of the endo-cavitary potential, and stimulation of the heart.

* * * * *